(12) United States Patent
Haughay, Jr. et al.

(10) Patent No.: US 10,353,952 B2
(45) Date of Patent: Jul. 16, 2019

(54) PERFORMANCE METADATA FOR MEDIA

(71) Applicant: Apple Inc., Cupertino, CA (US)

(72) Inventors: Allen P. Haughay, Jr., San Jose, CA (US); Benjamin Rottler, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 534 days.

(21) Appl. No.: 14/525,035

(22) Filed: Oct. 27, 2014

(65) Prior Publication Data

US 2015/0046814 A1 Feb. 12, 2015

Related U.S. Application Data

(62) Division of application No. 12/503,743, filed on Jul. 15, 2009, now Pat. No. 8,898,170.

(51) Int. Cl.
*G06F 16/638* (2019.01)
*A63B 24/00* (2006.01)
(Continued)

(52) U.S. Cl.
CPC ........ *G06F 16/639* (2019.01); *A63B 24/0062* (2013.01); *A63B 71/0622* (2013.01);
(Continued)

(58) Field of Classification Search
CPC combination set(s) only.
See application file for complete search history.

(56) References Cited

U.S. PATENT DOCUMENTS 4,649,552 A 3/1987 Yukawa 5,471,405 A 11/1995 Marsh
(Continued)

FOREIGN PATENT DOCUMENTS

EP 1847304 A1 10/2007
EP 1923103 A1 5/2008
(Continued)

OTHER PUBLICATIONS

Sasank Reddy, et al., "Lifetrak: Music in Tune With Your Life" XP002472329, Oct. 27, 2006, pp. 25-34.
(Continued)

*Primary Examiner* — Van H Oberly
(74) *Attorney, Agent, or Firm* — Womble Bond Dickinson (US) LLP

(57) ABSTRACT

Systems and methods for generating and using performance metadata associated with a media piece (e.g., music or video) are provided. An electronic device can monitor a user's workout performance while playing a particular media piece. Workout performance may include the user's rate of motion and/or one or more physiological metrics of the user. Based on the user's workout performance, the electronic device can create new or modify existing performance metadata associated with the media piece. In some embodiments, the performance metadata based on a particular user's workout performance in response to a media piece may be combined with collective performance metadata based on the workout performances of multiple users in response to the media piece. The combined performance metadata may then be stored as new collective metadata. Accordingly, the collective performance metadata can represent the average response to a media piece over multiple users.

22 Claims, 7 Drawing Sheets

(51) Int. Cl.
    *A63B 71/06*     (2006.01)
    *G06F 19/00*     (2018.01)
    *G06F 3/0482*     (2013.01)
    *G06F 3/0484*     (2013.01)

(52) U.S. Cl.
    CPC ........ *G06F 3/0482* (2013.01); *G06F 3/04842* (2013.01); *G06F 19/3481* (2013.01); *A63B 2071/0625* (2013.01); *A63B 2220/803* (2013.01); *A63B 2225/20* (2013.01); *A63B 2225/50* (2013.01); *A63B 2230/00* (2013.01)

(56) References Cited

U.S. PATENT DOCUMENTS

| | | |
|---|---|---|
| 6,013,007 A | 1/2000 | Root et al. |
| 6,032,108 A | 2/2000 | Seiple et al. |
| 6,135,951 A | 10/2000 | Richardson et al. |
| 6,192,340 B1 | 2/2001 | Abecassis |
| 6,357,147 B1 | 3/2002 | Darley et al. |
| 6,463,385 B1 | 10/2002 | Fry |
| 6,487,663 B1 | 11/2002 | Jaisimha et al. |
| 6,539,336 B1 | 3/2003 | Vock et al. |
| 6,560,903 B1 | 5/2003 | Darley |
| 6,582,342 B2 | 6/2003 | Kaufman |
| 6,619,835 B2 | 9/2003 | Kita |
| 6,716,139 B1 | 4/2004 | Hosseinzadeh-Dolkhani et al. |
| 6,790,178 B1 | 9/2004 | Mault et al. |
| 6,793,607 B2 | 9/2004 | Neil |
| 6,898,550 B1 | 5/2005 | Blackadar et al. |
| 7,030,735 B2 | 4/2006 | Chen |
| 7,062,225 B2 | 6/2006 | White |
| 7,171,331 B2 | 1/2007 | Vock et al. |
| 7,174,227 B2 | 2/2007 | Kobayashi et al. |
| 7,200,517 B2 | 4/2007 | Darley et al. |
| 7,251,454 B2 | 7/2007 | White |
| 7,278,966 B2 | 10/2007 | Hjelt et al. |
| 7,292,867 B2 | 11/2007 | Werner et al. |
| 7,353,139 B1 | 4/2008 | Burrell et al. |
| 7,454,002 B1 | 11/2008 | Gardner et al. |
| 7,519,327 B2 | 4/2009 | White |
| 7,521,623 B2 | 4/2009 | Bowen |
| 7,618,345 B2 | 11/2009 | Corbalis et al. |
| 7,670,263 B2 | 3/2010 | Ellis et al. |
| 2002/0077784 A1 | 6/2002 | Vock et al. |
| 2003/0097878 A1 | 5/2003 | Farringdon et al. |
| 2003/0208113 A1 | 11/2003 | Mault et al. |
| 2005/0172311 A1 | 8/2005 | Hjelt et al. |
| 2006/0169125 A1 | 8/2006 | Ashkenazi et al. |
| 2006/0265730 A1* | 11/2006 | Hays ................ G06F 17/30053 725/110 |
| 2007/0074619 A1 | 4/2007 | Vergo |
| 2007/0079691 A1 | 4/2007 | Turner |
| 2007/0118043 A1* | 5/2007 | Oliver ................ A61B 5/0245 600/519 |
| 2007/0162933 A1* | 7/2007 | Hays .................. G06F 16/4387 725/46 |
| 2007/0254271 A1 | 11/2007 | Burlik et al. |
| 2007/0271116 A1 | 11/2007 | Wysocki et al. |
| 2008/0000344 A1 | 1/2008 | Komori et al. |
| 2008/0076972 A1 | 3/2008 | Dorogusker et al. |
| 2008/0086318 A1 | 4/2008 | Gilley et al. |
| 2008/0096726 A1* | 4/2008 | Riley ................ A63B 24/0006 482/8 |
| 2008/0134862 A1 | 6/2008 | Lumme et al. |
| 2008/0162358 A1 | 7/2008 | Patsiokas et al. |
| 2008/0188354 A1 | 8/2008 | Pauws et al. |
| 2008/0236370 A1* | 10/2008 | Sasaki ................ A63B 71/0686 84/612 |
| 2009/0024233 A1 | 1/2009 | Shirai et al. |
| 2009/0044687 A1 | 2/2009 | Sorber |
| 2009/0063975 A1 | 3/2009 | Bull et al. |
| 2009/0070370 A1 | 3/2009 | Cunningham et al. |
| 2009/0100068 A1 | 4/2009 | Gauba et al. |
| 2009/0125609 A1 | 5/2009 | Wood et al. |
| 2009/0158155 A1 | 6/2009 | Quinn et al. |
| 2009/0205482 A1 | 8/2009 | Shirai |
| 2009/0326949 A1 | 12/2009 | Douthitt et al. |
| 2010/0273610 A1* | 10/2010 | Johnson ............ A63B 24/0075 482/9 |

FOREIGN PATENT DOCUMENTS

| | | |
|---|---|---|
| JP | 11-242686 | 9/1999 |
| JP | 2006239397 A | 9/2006 |
| JP | 2006239398 A | 9/2006 |
| JP | 2008015595 | 1/2008 |
| JP | 2008015595 A | 1/2008 |
| KR | 1999-0073234 | 10/1999 |
| WO | 02/093272 | 11/2002 |
| WO | 2007144030 A1 | 12/2007 |

OTHER PUBLICATIONS

Myung-Kyung Suh et al., "Interval Training Guidance System with Music and Wireless Group Exercise Motivations" Industrial Embedded Systems, 2009, IEEE International Symposium ON, Piscataway, NJ, XP031504608, Jul. 8, 2009, pp. 110-119.

Ericsson Inc. "Cellular Phone With Integrated MP3 Player." Research Disclosure Journal Number 41815, Research Disclosue Database No. 418015 (Feb. 1999).

Menta, "1200 Song MP3 Portable is a Milestone Player." http://www.mp3newswire.net/stories/personaljuke.html (retrieved Jul. 17, 2010).

Creative NOMAD® Digital Audio Player User Guide.
Creative NOMAD® II Getting Started Guide.
Rio 500 Getting Started Guide.
Rio PMP300 User's Guide (1998).

\* cited by examiner

| | 410 | 420 | 430 | 440 | 450 | 460 | 470 | 482 | 484 | |
|---|---|---|---|---|---|---|---|---|---|---|
| | ID | Media Type | Name | Artist | Album | Track Length | BPM | Average Pace | Average Performance Compared to Target Performance | ... |
| 401 | | | | | | | | | | |
| 402 | 102894 | Audio | Black Dog | Led Zeppelin | Led Zeppelin IV | 4:54 | 95 | 8:42 | +1% | ... |
| 403 | 102895 | Audio | Get off of My Cloud | The Rolling Stones | December's Children | 2:55 | 109 | 8:11 | -2% | ... |
| | 102896 | Audio | Gimme Shelter | The Rolling Stones | Let it Bleed | 4:31 | 102 | 8:18 | -1% | ... |
| 404 | 102897 | Audio | Angie | The Rolling Stones | Goats Head Soup | 4:33 | 83 | 9:07 | +4% | ... |
| 405 | 102898 | Audio | Immigrant Song | Led Zeppelin | Led Zeppelin III | 2:25 | 115 | 7:49 | -2% | ... |
| | 102899 | Video | Stairway to Heaven | Led Zeppelin | Led Zeppelin IV | 8:00 | 78 | 9:35 | +3% | ... |
| 406 | ... | ... | ... | ... | ... | ... | ... | ... | ... | ... |

| | ID | Media Type | Name | Artist | Album | Length | BPM | Segment 1 | | Segment 2 | | ... |
|---|---|---|---|---|---|---|---|---|---|---|---|---|
| | | | | | | | | Average Pace | Comp. to Target | Average Pace | Comp. to Target | |
| 502 | 102894 | Audio | Black Dog | Led Zeppelin | Led Zeppelin IV | 4:54 | 95 | 8:42 | +1% | 8:26 | 0% | ... |
| 503 | 102895 | Audio | Get off of My Cloud | The Rolling Stones | December's Children | 2:55 | 109 | 8:11 | -2% | 8:14 | -1% | ... |
| | 102896 | Audio | Gimme Shelter | The Rolling Stones | Let It Bleed | 4:31 | 102 | 8:18 | -1% | 9:40 | +2% | ... |
| | 102897 | Audio | Angie | The Rolling Stones | Goats Head Soup | 4:33 | 83 | 9:07 | +4% | 8:53 | +2% | ... |
| 504 | 102898 | Audio | Immigrant Song | Led Zeppelin | Led Zeppelin III | 2:25 | 115 | 7:49 | -2% | 7:53 | -2% | ... |
| 505 | 102899 | Video | Stairway to Heaven | Led Zeppelin | Led Zeppelin IV | 8:00 | 78 | 9:35 | +3% | 9:10 | +1% | ... |
| 506 | ... | ... | ... | ... | ... | ... | ... | ... | ... | ... | ... | ... |

PERFORMANCE METADATA FOR MEDIA

This application is a divisional of co-pending U.S. patent application Ser. No. 12/503,743, filed on Jul. 15, 2009

BACKGROUND OF THE INVENTION

This is directed to performance metadata associated with media pieces. In particular, this is directed to systems and methods for generating and using performance metadata.

Some traditional electronic devices store metadata representing the beats per minute (BPM) of a song. For example, each song may be associated with a BPM metadata tag which represents the average BPM of the song. Traditional electronic devices may then use this BPM metadata to compile workout playlists based on a selected exercise plan (e.g., interval training or hill training). However, such BPM metadata may not be a completely accurate measure for stimulating workout responses in users because a song might include musical features other than BPM which influence users' responses.

SUMMARY OF THE INVENTION

This is directed to systems and methods for generating and using performance metadata associated with a media piece (e.g., music or video). An electronic device can monitor a use workout performance while playing a particular media piece. Workout performance may include the user's rate of motion and/or one or more physiological metrics of the user. Based on the user's workout performance, the electronic device can create new or modify existing performance metadata associated with the media piece.

In some embodiments, the performance metadata based on a particular user's workout performance in response to a media piece may be combined with collective performance metadata based on the workout performances of multiple users in response to the media piece. The combined performance metadata may then be stored as new collective metadata. Accordingly, the collective performance metadata can represent the average response to a media piece over multiple users.

In some embodiments, different performance metadata can be generated for different segments of a media piece (e.g., five second intervals). In such embodiments, the performance metadata for a particular segment may then be combined with collective performance metadata associated with that segment.

In some embodiments, an electronic device can receive an input from a user representing the effectiveness of a workout, and performance metadata can be generated based on the user's workout performance and the received user input. In such embodiments, the performance metadata generated based on workout performance and a received user input may than be combined with collective performance metadata.

BRIEF DESCRIPTION OF THE DRAWINGS

The above and other features of the present invention, its nature and various advantages will be more apparent upon consideration of the following detailed description, taken in conjunction with the accompanying drawings in which:

FIG. 4 is a schematic view of an illustrative database for staring performance metadata in accordance with one embodiment of the invention;

FIG. 5 is a schematic view of an illustrative database for storing performance metadata in accordance with one embodiment of the invention;

DETAILED DESCRIPTION

This is directed to systems and methods for generating performance metadata associated with a media piece. An electronic device can monitor a user's workout performance while playing a particular media piece. Media piece may include a song, a music video, or any other suitable audio and/or visual recording. For example, an electronic device can monitor a user's workout performance while playing a song and generate performance metadata associated with that song.

Workout performance may include the user's rate of motion (e.g., pace or speed). For example, a device can include, or be coupled with, a sensor for measuring the user's rate of motion (e.g., a motion sensing component or positioning circuitry). In some embodiments, workout performance may include one or more physiological metrics of the user (e.g., heart rate). For example, a device can include, or be coupled with, a physiological sensor for measuring one or more physiological metrics of the user (e.g., a heart rate sensor, a pulse waveform sensor, a respiration sensor, a galvanic skin response sensor, a temperature sensor). In some embodiments, a device may include communications circuitry for communicating with an external device or sensor for measuring the user's rate of motion or a device or sensor for measuring one or more physiological metrics of the user.

Based on the user's workout performance, the electronic device can create new performance metadata associated with the media piece or modify existing performance metadata associated with the media piece. For example, a device can create new performance metadata associated with a media piece if there is no preexisting performance metadata associated with the media piece. If there is preexisting performance metadata associated with a media piece, the device can modify the existing performance metadata to incorporate any new information from monitoring a user's workout.

Figure 1:
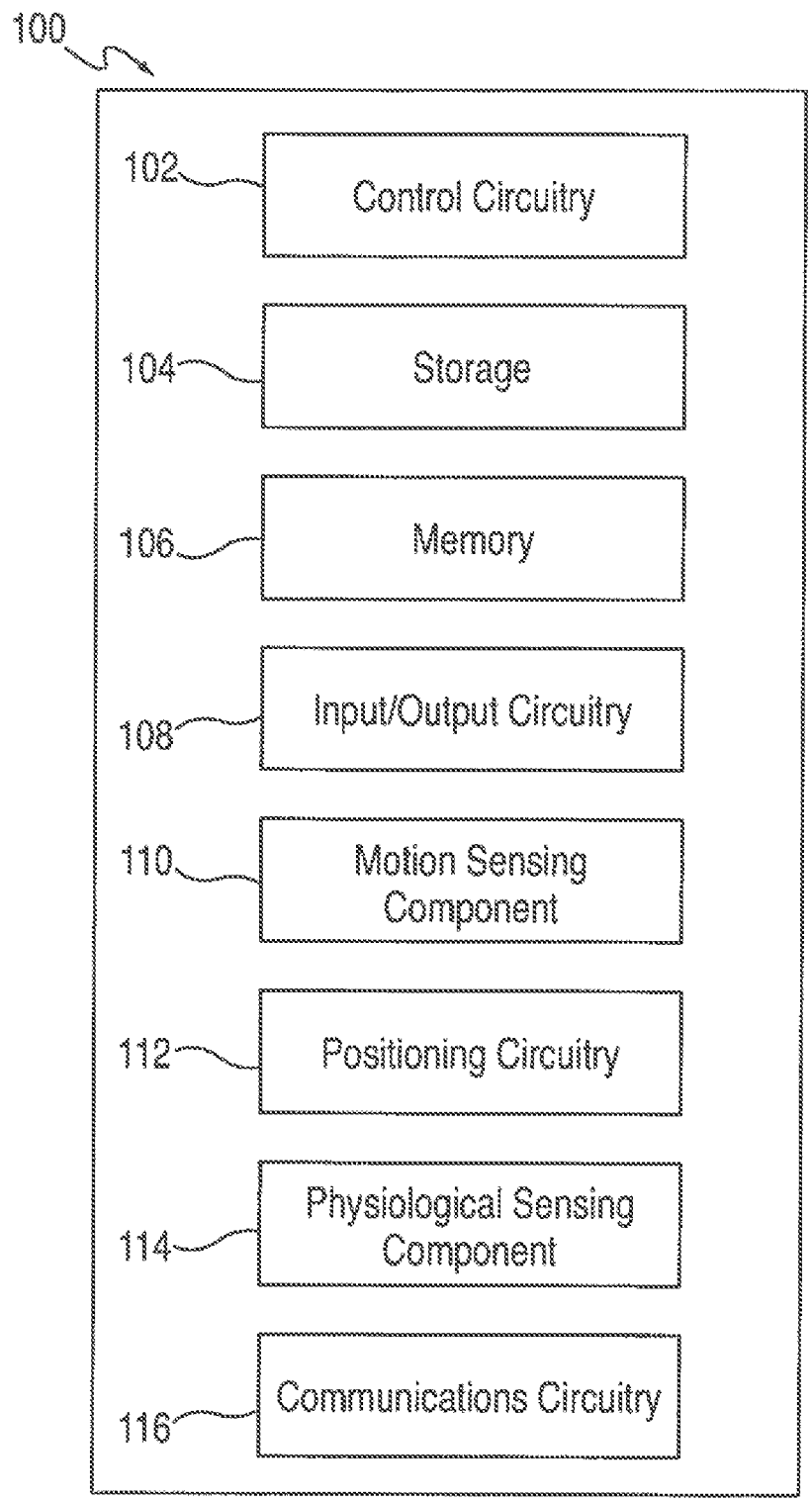
FIG. 1 is a schematic view of an illustrative electronic device for generating performance metadata in accordance with one embodiment of the invention.

FIG. 1 is a schematic view of an illustrative electronic device for generating performance metadata in accordance with one embodiment of the invention. Electronic device 100 can include control circuitry 102, storage 104, memory 106, input/output circuitry 108, motion sensing component 110, positioning circuitry 112, physiological sensing component 114, and communications circuitry 116. In some embodiments, one or more of the components of electronic device 100 can be combined or omitted. For example, storage 104 and memory 106 can be combined into a single mechanism for storing data. In some embodiments, electronic device 100 can include other components not combined or included in those shown in FIG. 1, such as a power supply (e.g., a battery or kinetics), a display, a bus, or an input mechanism. In some embodiments, electronic device 100 can include several instances or the components shown in FIG. 1 but, for the sake of simplicity, only one of each of the components is shown in FIG. 1.

Electronic device 100 can include any suitable type of electronic device operative to provide media pieces. For example, electronic device 100 can include a media player such as an Ipod® available by Apple Inc., of Cupertino, Calif., a cellular telephone, a personal e-mail or messaging device (e.g., a Blackberry® or a Sidekick®, an iPhone® available from Apple Inc., pocket-sized personal computers, personal digital assistants (PDAs), a laptop computer, a cyclocomputer, a music recorder, a video recorder, a camera, and any other suitable electronic device. In some cases, electronic device 100 can perform a single function (e.g., a device dedicated to playing music) and in other cases, electronic device 100 can perform multiple functions (e.g., a device that plays music, displays video, stores pictures, and receives and transmits telephone calls).

Control circuitry 102 can include any processing circuitry or processor operative to control the operations and performance of an electronic device of the type of electronic device 100. Storage 104 and memory 106, which can be combined can include, for example, one or more storage mediums or memory used in an electronic device of the type of electronic device 100. In particular, storage 104 and memory 106 can store information related to per metadata such as information representing a user's rate of motion of physiological metrics while a media piece is being played. The stored information can then be used to generate performance metadata after the entire media piece, or a segment of the media piece, has finished playing. In some embodiments, storage 104 and memory 106 can store performance metadata related to only the user of device 100. In some embodiments, storage 104 and memory 106 can store collective performance metadata related to multiple users (e.g., the user of device 100 and other users with devices similar to device 100). In some embodiments, storage 104 and memory 106 may also store media pieces associated with performance metadata stored thereon. Input/output circuitry 108 can be operative to convert (and encode/decode, if necessary) analog signals and other signals into digital data, for example in any manner typical of an electronic device of the type of electronic device 100. Electronic device 100 can include any suitable mechanism or component for allowing a user to provide inputs to input/output circuitry 108, and any suitable circuitry for providing outputs to a use (e.g., audio output circuitry or display circuitry).

Motion sensing component 110 can be operative to detect movements of electronic device 100. In some embodiments, motion sensing component 110 can include one or more three-axes acceleration motion sensing components (e.g., an accelerometer) operative to detect linear acceleration in three directions (i.e., the x or left/right direction, the y or up/down direction, and the z or forward/backward direction). As another example, motion sensing component 110 can include one or more two-axis acceleration motion sensing components which can be operative to detect linear acceleration only along each of x or left/right and y or up/down directions (or any other pair of directions). In some embodiments, motion sensing component 110 can include an electrostatic capacitance (capacitance-coupling) accelerometer that is based on silicon micro-machined MEMS (Micro Electro Mechanical Systems) technology, a piezoelectric type accelerometer, a piezoresistance type accelerometer, or any other suitable accelerometer.

In some embodiments, motion sensing component 110 can directly detect rotation, rotational movement, angular displacement, tilt, position, orientation, motion along a nonlinear (e.g., arcuate) path, or any other non-linear motions. For example, if motion sensing component 110 is a linear motion sensing component, additional processing can be used to indirectly detect some or all of the non-linear motions. For example, by comparing the linear output of the motion sensing component with a gravity vector (i.e., a static acceleration), motion sensing component 110 can calculate the tilt of electronic device 100 with respect to the y-axis. In some embodiments, motion sensing component 110 can, instead or in addition, include one or more gyro-motion sensing components or gyroscopes for directly detecting rotational movement. For example, motion sensing component 110 can include a rotating or vibrating element. As another example, motion sensing component 110 can include a magnometer operative to detect the orientation of the device relative a magnetic north pole. The electronic device can monitor changes in the output of the magnometer to detect rotations of the device.

Electronic device 100 can include positioning circuitry 112 for determining the current position of electronic device 100, and can be operative to update the current position at any suitable rate, including at relatively high rates to provide an estimation of speed and distance traveled. In some embodiments, positioning circuitry 112 can include a global positioning system ("GPS") receiver for accessing a GPS application function call that returns the geographic coordinates (i.e., the geographic location) of the device. The geographic coordinates can be fundamentally, alternatively, or additionally derived from any suitable trilateration or triangulation technique. For example, the device can determine its location using various measurements (e.g., signal-to-noise ratio ("SNR") or signal strength) of a network signal (e.g., a cellular telephone network signal) associated with the device. For example, a radio frequency ("RF") triangulation detector or sensor integrated with or connected to the electronic device can determine the approximate location of the device. The device's approximate location can be determined based on various measurements of the device's own network signal, such as; (1) the angle of the signal's approach to or from one or more cellular towers, (2) the amount of time for the signal to reach one or more cellular towers or the user's device, (3) the strength of the signal when it reaches one or more towers or the user's device, or any combination of the aforementioned measurements, for example. Other forms of wireless-assisted GPS (sometimes referred to herein as enhanced GPS or A-GPS) can also be used to determine the current position of electronic device 100. Instead or in addition, positioning circuitry 112 can determine the location of the device based on a wireless network or access point that is in range or a wireless network or access point to which the device is currently connected. For example, because wireless networks have a finite range, a network that is in range of the device can indicate that the device is located in the approximate geographic location of the wireless network.

Physiological sensing component 114 can be operative to detect one or more physiological metrics of a user. For example, physiological sensing component 114 may be operative to detect one or more physiological metrics of a user operating device 100. Physiological sensing component 114 can include a sensor operative to detect a user's heart rate, pulse waveform, breathing rate, blood-oxygen content, galvanic skin response, temperature, heat flux, any other suitable physiological metric, or any combination thereof. For example, physiological sensing component 114 can include a heart rate sensor, a pulse waveform sensor, a respiration sensor, a galvanic skin response sensor, a temperature sensor (e.g., an infrared photodetector), an optical sensor (e.g., a visible or infrared light source and photodetector), any other suitable physiological sensor, or any combination thereof. In some embodiments, physiological sensing component 114 may include one or more electrical contacts for electrically coupling with a user's body. Such sensors can be exposed to the external environment or disposed under an electrically, optically, and/or thermally conductive material so that the contact can obtain physiological signals through the material. A more detailed description of suitable components for detecting physiological metrics with electronic devices can be found in U.S. patent application Ser. No. 11/729,075, entitled "Integrated Sensors for Tracking Performance Metrics" and filed on Mar. 27, 2007, which is incorporated by reference herein in its entirety.

Communications circuitry 116 can include any suitable communications circuitry operative to connect to a communications network and to transmit communications (e.g., voice or data) from device 100 to other devices within the communications network. Communications circuitry 116 can be operative to interface with the communications network using any suitable communications protocol such as, for example, Wi-Fi (e.g., a 802.11 protocol), Bluetooth®, radio frequency systems (e.g., 900 MHz, 1.4 GHz, and 5.6 GHz communication systems), cellular networks (e.g., GSM, AMPS, GPRS, CDMA, EV-DO, EDGE, 3GSM, DECT, IS-136/TMDA, iDen, LTE or any other suitable cellular network or protocol), infrared, TCP/IP (e.g., any of the protocols used in each of the TCP/IP layers), HTTP, BitTorrent, FTP, RTP, RTSP, SSH, Voice over IP (VOIP), any other communications protocol, or any combination thereof. In some embodiments, communications circuitry 116 can be operative to provide wired communications paths for electronic device 100.

In some embodiments, communications circuitry 116 can interface electronic device 100 with an external device or sensor for measuring the user's rate of motion. For example, communications circuitry 116 can interface electronic device 100 with a motion sensor attached to or incorporated within, the user's body or clothing (e.g., a motion sensor similar to the sensor from the Nike+iPod Sport Kit sold by Apple Inc. of Cupertino, Calif. and Nike Inc. of Beaverton, Oreg.). In another example, communications circuitry 116 can interface device 100 with exercise equipment (e.g., a treadmill or elliptical machine) to determine a user's rate of motion. A more detailed description of suitable exercise equipment for communicating with electronic devices can be found in U.S. patent application Ser. No. 12/238,436, entitled "Interfacing Portable Media Devices and Sports Equipment" and filed on Sep. 26, 2000, which is incorporated by reference herein in its entirety.

In some embodiments, communications circuitry 116 can interface electronic device 100 with an external device or sensor for measuring one or more physiological metrics of the user. For example, communications circuitry 116 can interface electronic device 100 with a physiological sensor attached to or incorporated within the user's body or clothing (e.g., a piece of clothing with integrated heart rate sensors similar to the NuMetrex clothing line from Textronics, Inc. of Wilmington, Del.).

In some embodiments, communications circuitry 116 can be operative to interface electronic device 100 with a host device (e.g., a host computer) for data transfers, synchronizing (i.e., "synching") the device, software or firmware updates, providing performance information to a remote source (e.g., providing workout performance metadata to a remote server) or performing any other suitable operation that can require electronic device 100 to be coupled to a host device. Several electronic devices 100 can be coupled to a single host device using the host device as a server and, instead or in addition, electronic device 100 can be coupled to several host devices (e.g., for each of the several host devices to serve as a backup for data stored in electronic device 100).

Figure 2:
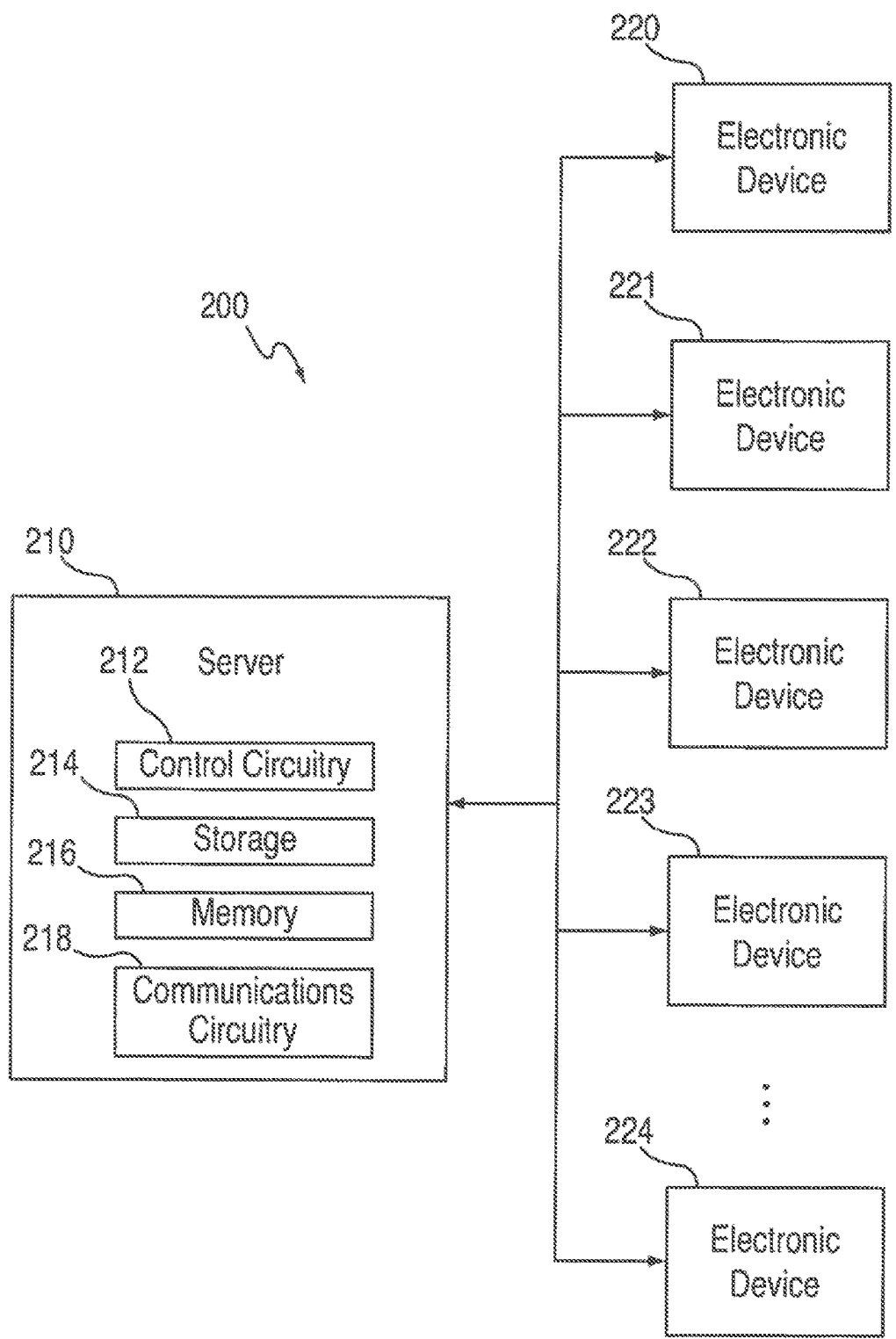
FIG. 2 is a schematic view of an illustrative system for generating collective performance metadata in accordance with one embodiment of the invention.

Collective performance metadata may be based on performance metadata generated by multiple user devices (e.g., multiple iterations of device 100). In some embodiments, a master version of collective performance metadata may be stored on a central system or server. FIG. 2 is a schematic view of system 200 for generating collective performance metadata in accordance with one embodiment of the invention. System 200 may include server 210 and electronic devices 220-224. Electronic devices 220-224 may include any suitable devices for generating workout performance metadata (see, e.g., device 100). Server 210 may include any suitable device or computer for communicating with electronic devices 220-224. For example, server 210 may include an internet server for communicating with electronic devices 220-224 and storing data received from devices 220-224. Server 210 and electronic devices 220-224 may communicate together using any suitable communications protocol. For example, server 210 and devices 220-224 may communicate using any protocol supported by communications circuitry in each of devices 220-224 (see, e.g., communications circuitry 116 in device 100). Server 210 and/or devices 220-224 may communicate using a protocol such as for example, Wi-Fi (e.g., a 802.11 protocol), Bluetooth®, radio frequency systems (e.g., 900 MHz, 1.4 GHz, and 5.6 GHz communication systems), cellular networks (e.g., GSM, AMPS, GPRS, CDMA, EV-DO, EDGE, 3GSM, DECT, IS-136/TDMA, iDen, LTE or any other suitable cellular network or protocol), infrared, TCP/IP (e.g., any of the protocols used in each of the TCP/IP layers), HTTP, BitTorrent, FTP, RTP, RTSP, SSH, Voice over IP (VOIP), any other communications protocol, or any combination thereof.

Server 210 may include control circuitry 212, storage 214, memory 216, and communications circuitry 218, which may be substantially similar to, respectively, control circuitry 102, storage 104, memory 106, and communications circuitry 116 of device 100. Accordingly, the previous discussion of the latter can be applied to the former. Control circuitry 212 can include any suitable processing circuitry or processor operative to control the operations and performance of server 210. Communications circuitry 218 may include any suitable communications circuitry operative to connect to a communications network, transmit communications (e.g., voice or data) to devices 220-224, and receive communications (e.g., voice or data) from devices 220-224. Communications circuitry 218 may support any suitable communications protocol so that, as previously discussed, server 210 may communicate using any suitable communications protocol.

Server 210 may include storage 214 and/or memory 216 for storing data received from devices 220-224. Storage 214 and memory 216, which can be combined can include, for example, one or more storage mediums or memory used in a server of the type of server 210. In particular, storage 214 and memory 216 can store collective performance metadata related to the users of devices 220-224. In some embodiments, storage 714 and memory 216 may also store media pieces associated with performance metadata stored thereon.

In some embodiments, an electronic device or a server may stored a master version of collective performance metadata. The master version of collective performance metadata may be used to coordinate the generation and dissemination of collective performance metadata amongst multiple electronic devices. For example, server 210 may store a master version of collective performance metadata that is based on performance metadata received from devices 220-224. Each of devices 220-224 can transmit performance metadata to server 210 and then server 210 can update the collective performance metadata based on the metadata received from each device. For example, each of devices 220-224 may transmit performance metadata to server 210 when the device synchronizes with server 210. In some embodiments, server 210 may update the master version of collective metadata each time new performance metadata is received. For example, if server 210 receives new performance metadata from one of devices 220-224 (e.g., based, on the workout performance of a device's user), server 210 may update the collective metadata. In some embodiments, server 210 may temporarily store all received performance metadata and then periodically update the collective metadata to incorporate all of the received metadata.

In some embodiments, one or more of devices 220-224 may store local versions of collective performance metadata. For example, one or more of devices 220-224 may store local versions of collective performance metadata so that each device can select media pieces based on the metadata (see, e.g., process 700 shown in FIG. 7). The collective performance metadata stored in a device may be received from a server or another electronic device. For example, server 210 may transmit collective performance metadata to one or more of devices 220-224, and the devices may store a local version of the collective metadata in storage or memory (see, e.g., storage 104 and memory 106). In some embodiments, server 210 may periodically retransmit collective performance metadata to one or more of devices 220-224 so that the version of collective performance metadata stored on devices 220-224 does not become too outdated. For example, server 210 may transmit new collective performance metadata to a device every time that the device synchronizes with server 210.

In some embodiments, a server or electronic device may stream collective performance metadata to one or more of devices, and the devices may not need to store local versions. For example, server 210 may stream collective performance metadata to one or more of devices 220-224 so that the devices can select media pieces based on the metadata (see, e.g., process 700 shown in FIG. 7). However, in embodiments where collective performance metadata is streamed to a device, the device may need to be in communication with the server or other device to select media pieces based on the streaming metadata.

While the embodiment shown in FIG. 2 includes electronic devices 220-224 coupling with server 210 and each other, it is understood that, in some embodiments, each of devices 220-224 may use a host device (e.g., a personal computer) to couple with server 210 and each other. In such embodiments, it may be advantageous to provide local versions of collective performance metadata because the device may not always be coupled with the host device and, therefore, may not always be in communication with a server or other device that stores the master version of collective performance metadata.

Moreover, while the embodiment shown in FIG. 2 includes server 210, it is understood that electronic devices 220-224 may communicate amongst each other without using a server in some embodiments. For example, devices 220-224 may form a peer-to-peer network that does not require a server. In some embodiments, a global or master version of collective performance metadata may be stored on one or more of devices 220-224 rather than a server.

Figure 3:
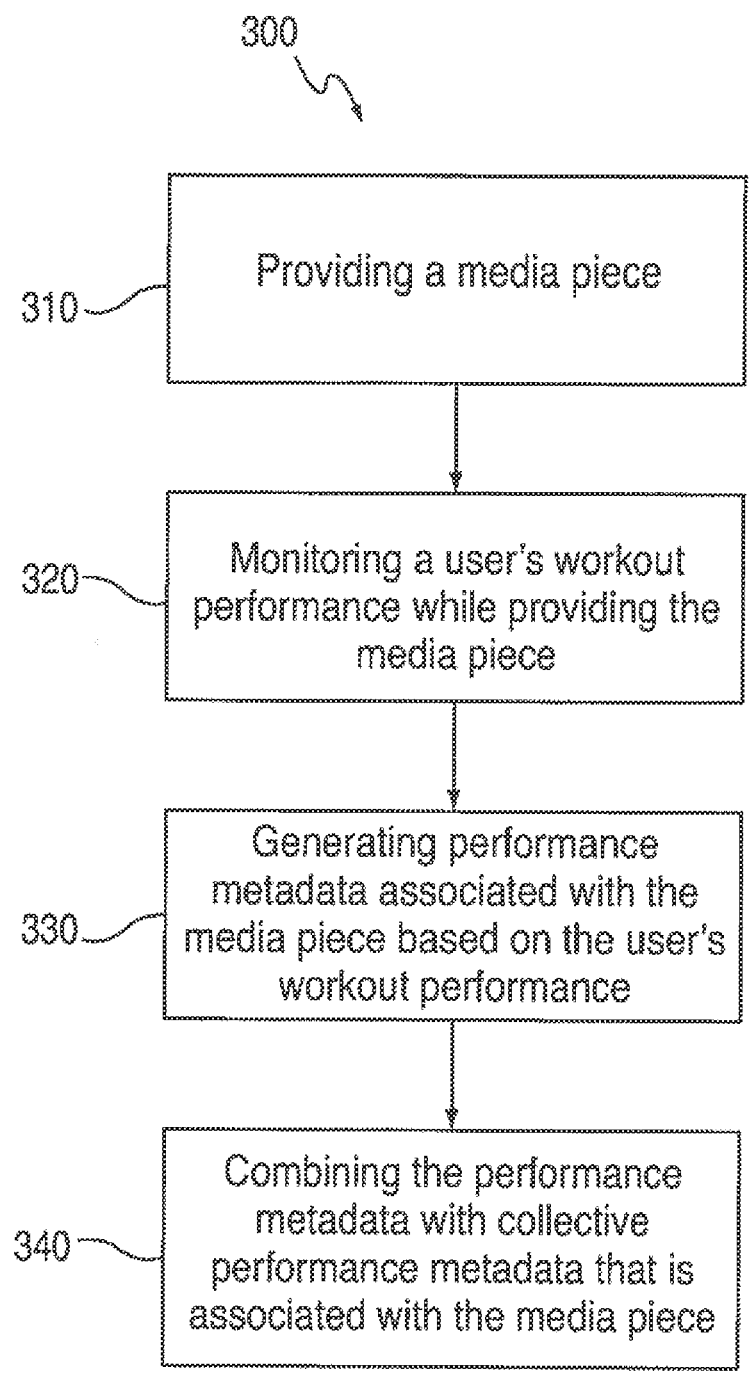
FIG. 3 is a flowchart of an illustrative process for generating performance metadata in accordance with one embodiment of the invention.

FIG. 3 is a flowchart of illustrative process 300 for generating performance metadata in accordance with one embodiment of the invention. Process 300 can be performed by a single device (e.g., device 100 or one of devices 220-224), multiple devices (e.g., two of devices 220-224), a server and a device (e.g., server 210 and one of devices 220-224), or any suitable combination of servers and devices. Process 300 can begin at block 310.

At block 310, a media piece can be provided. The media piece can be provided by any suitable device (see, e.g., device 100 or devices 220-224). As previously discussed, a media piece can include a song, a music video, or any other suitable audio and/or visual recording. For example, a device can provide a song to its user. The media piece can be provided through input/output circuitry in a device (see, e.g., input/output circuitry 108 in device 100). For example, the media piece can be provided through one or more speakers integrated into the device, one or more speakers coupled with the device, headphones coupled with the device, a display integrated into the device, one or more displays coupled with the device, any other suitable input/output circuitry, or any combination thereof.

At block 320, a user's workout performance can be monitored while the media piece is provided. The workout performance can be monitored by any suitable device (see, e.g., device 100 or devices 220-224). As previously discussed, a user's workout performance may include the user's rate of motion (e.g., pace or speed), one or more physiological metrics of the user (e.g., heart rate, pulse waveform, breathing rate, blood-oxygen content, galvanic skin response, temperature, or heat flux), any other suitable measure of a user's workout performance, or any combination thereof. Any suitable sensor, whether integrated into a device or coupled with a device, can be used to measure workout performance at block 320 (see, e.g., motion sensing component 110, positioning circuitry 112, and physiological sensing component 114 of device 100). In some embodiments, a device may measure a user's pace at block 320 using a motion sensing component (e.g., component 110 of device 100). In some embodiments, a device may temporarily store information related to workout performance while the media piece is provided. For example, a device may temporarily store workout performance measurements taken at regular intervals while the media piece was provided.

At block 330, performance metadata associated with the media piece can be generated based on the user's workout performance. The performance metadata can be generated by any suitable device (see, e.g., device 100 or devices 220-224). Performance metadata can be generated at block 330 that represents the user's workout performance while the media piece was provided. Accordingly, performance metadata may represent the effect that the provided media piece had on the user's workout (e.g., the user's response). Performance metadata can include any suitable datum representing a measurement of a user's workout performance.

For example, performance metadata can include the user's pace (e.g., time per distance), speed (e.g., distance per time), heart rate, pulse waveform, breathing rate, blood-oxygen content, galvanic skin response, temperature, or heat flux, any other suitable measure of a user's workout performance, or any combination thereof.

In some embodiments, performance metadata may be based at least partially on an exercise plan (e.g., an exercise activity profile). For example, a user may workout according to an exercise plan of a particular type (e.g., Fartlek Interval or Intense Interval), and a device may generate performance metadata based on both the user's workout performance and the type of exercise plan. In such embodiments, performance metadata may represent whether a media piece is effective for a particular type of exercise plan.

In some embodiments, performance metadata may be based at least partially on an exercise plan that includes one or more targets (e.g., target running paces or target heart rates). For example, a user may workout according to an exercise plan that includes a target, and a device may generate performance metadata based on the user's workout performance in relation to the target. In such embodiments, performance metadata may represent whether a media piece is effective at helping a user achieve targets in connection with exercise plans.

In some embodiments, an exercise plan can include multiple phases and performance metadata may be based at least partially on a phase of the exercise plan. For example, an exercise plan can include a warm-up phase, a cool-down phase, an intense phase, a recovery phase, any other suitable type of phase, or any combination thereof. In some embodiments, performance metadata may be based at least partially on the phase of an exercise plan during which the associated media piece is provided. For example, performance metadata may be based on the user's workout performance when the associated media piece is provided during a particular phase of an exercise plan. Accordingly, performance metadata may represent whether a media piece is effective at a particular phase in an exercise plan. For example, performance metadata may represent whether a media piece is effective during a warm-up phase, a cool-down phase, or any other phase of an exercise plan.

In some embodiments, performance metadata may be based on the user's average workout performance while the media piece was provided. For example, performance metadata generated at block 330 may be based on the average of multiple workout performance measurements taken while the media piece was provided. In some embodiments, performance metadata may include multiple workout performance measurements associated with different segments of a media piece. For example, performance metadata generated at block 330 may include a different workout performance measurement for each segment of a media piece (e.g., each five second segment).

At block 340, performance metadata can be combined with collective performance metadata that is associated with the media piece. The performance metadata can be combined with collective performance metadata by any suitable device (see, e.g., device 100 or devices 220-224). As previously discussed, the collective performance metadata may represent the workout performance of other users in response to the media piece (e.g., how other users reacted to the media piece). Combining the performance metadata with collective performance metadata may generate new collective performance metadata that also represents the monitoring performed at block 320.

In some embodiments, the performance metadata may be combined with collective performance metadata that is based on the workout performance of similar users. For example, different to of collective performance metadata may exist for different types of users and performance metadata representing a user's workout performance may only be combined with collective performance metadata representing the workouts of other users of a similar type. User types can be formed based on any suitable user characteristic such as, for example, workout experience, average workout performance (e.g., average pace), general fitness level, age, weight, sex, or any other suitable characteristic, or any combination thereof.

In some embodiments, one or more characteristics of the user may affect how her performance metadata is combined with collective performance metadata. For example, the user's performance metadata may be adjusted based on one or more characteristics of the user before it is combined with collective performance metadata. For example, if a user typically achieves very high levels of workout performance (e.g., the user is a fast runner), performance metadata based on the user may be reduced (e.g., average pace adjusted to be slower) before it is combined with collective performance metadata. The user's performance metadata may be adjusted based on any suitable user characteristic such as for example, workout experience, average workout performance (e.g., average pace), general fitness level, age, weight, sex, or any other suitable characteristic, or any combination thereof. Such adjustment may facilitate the creation of collective performance metadata that more accurately represents the workout performance of average users. However, in embodiments where collective performance metadata is based on a substantial number of users, the collective performance metadata may be naturally averaged over all of the users.

In some embodiments, process 300 can include uploading information about a user's workout performance to a server (see, e.g., server 210) at any point after block 320. Moreover, block 330 and/or block 340 can be performed by the server in some embodiments. For example, process 300 can include uploading information about a user's workout performance to a server after block 320, and block 330 and block 340 may be performed by the server. In another example, process 300 can include uploading performance metadata to a server after block 330, and block 340 may be performed by the server. In some embodiments, it may be advantageous for a server to perform block 340 because the server may coordinate or have stored thereon a master version of collective performance metadata.

Performance metadata may be stored in one or more databases. In some embodiments, performance metadata may be stored in a database along with other metadata associated with media pieces. For example, performance metadata may be stored in a database along with other metadata representing information about media pieces (e.g., title, artist, track length, track number, album, genre, or composer). FIG. 4 is a schematic view of database 400 for storing performance metadata in accordance with one embodiment of the invention. Database 400 can be stored on any suitable device (e.g., device 100 or devices 220-224) or any suitable server (e.g., server 210) In some embodiments, different devices or servers may store different versions of database 400 (e.g., master and/or local versions).

Database 400 can include metadata associated with numerous media pieces. For example, database 400 can include the metadata associated with all the media pieces in a library. Database 400 can include a separate record for each media piece, and each record can be represented by a row in FIG. 4. For example, database 400 can include illustrative records 401-406, and each record may represent a different media piece.

Database 400 can include numerous fields for storing and organizing information about each record. For example, database 400 can include fields corresponding to identification metadata (e.g., information indexing media pieces or representing where media pieces are stored), attribute metadata (e.g., general information about media pieces such as media type, title, or artist), performance metadata, or any other information or metadata associated with media pieces.

Database 400 can include one or more fields for storing identification metadata representing the media pieces. For example, field 410 can include index numbers, and each index number can represent a media piece. Identification metadata can be used to access a database record or a media piece associated with a database record. In some embodiments, field 410 can include file system data associated with a media piece. For example, field 410 could represent the address in a file, system where a media piece is stored (e.g., a file allocation table address). Identification metadata stored in field 410 may be updated by a system or device storing database 400 as records are added or removed from the database.

Database 400 can include one or more fields for storing attribute metadata representing general information about the media pieces (see, e.g., fields 420, 430, 440, 450, 460, and 470). Database 400 can include a field for storing media type metadata associated with a media piece. For example, field 420 may store metadata representing the media type of a media piece (e.g., audio or video). In some embodiments, field 420 may store metadata representing the content of a media piece. For example, field 420 may store metadata indicating whether a media piece is a song, chapter of an audio book, music video of a song, episode of a television show, movie, or any other suitable media content. Database 400 can include fields for storing metadata representing the title or creator of a media piece. For example, field 430 may store metadata representing the title of a media piece, and field 440 may store metadata representing the artist that created the media piece. Database 400 can include a field for storing metadata representing media piece groupings. For example, field 450 may store metadata representing a group of media pieces that includes a media piece. In some embodiments, if a media piece is a song, the corresponding entry in field 450 may store metadata representing an album that includes the song. In some embodiments, if a media piece is an episode of a television show, the corresponding entry in field 450 may store metadata representing a season that includes the episode. Database 400 can include a field for storing metadata representing media piece length. For example, field 460 may store metadata representing the length of a media piece. Database 400 can include a field for storing metadata representing audio metrics of a media piece (e.g., beats per minute, time signature, or frequency components). For example, field 470 may store metadata representing the average heats per minute (BPM) of a media piece. In some embodiments, a media piece may be analyzed to determine one or more audio metrics when a new record is created in database 400. In other embodiments, one or more audio metrics may be received from another device (e.g., a music library server) or manually inputted when a new record is created in database 400.

Database 480 can include one or more fields for storing performance metadata representing workout performance associated with the media pieces (see, e.g., group 480 of fields 482 and 484). In some embodiments, database 400 can include one or more fields for storing performance metadata based on the workout performance of one or more users. For example, field 482 may store metadata representing the average running pace of one or more users when a particular media piece is provided. In some embodiments, database 400 can include one or more fields for storing performance metadata based on the workout performance of one or more users relative to their respective exercise plans (e.g., exercise activity profiles). As previously discussed with respect to block 330 of process 300, performance metadata may be based at least partially on an exercise plan that includes one or more targets. Accordingly, performance metadata based at least partially on workout performance relative to one or more targets may be stored in database 400. For example, field 484 may store metadata representing the average performance of one or more users relative to their respective exercise plans when a particular media piece is provided. In the embodiment shown in FIG. 4, each entry of field 484 can include a percentage value that reflects whether, and to what extent, one or more users exceed their exercise targets (e.g., positive percentage) or fall short of their exercise targets (e.g., negative percentage) when a particular media piece is provided.

In some embodiments, performance metadata may be based at least partially on a type of exercise plan. As previously discussed with respect to block 330 of process 300, performance metadata may be based at least partially on the type of exercise plan a user is performing when her performance is monitored. In some embodiments, a database can include different fields of performance metadata corresponding to different types of exercise plans. Accordingly, each record may include different metadata representing how the associated media piece affects the user's workout performance when it is provided during each type of exercise plan. For example, each record may include metadata representing how a media piece affects the user's workout performance when it is provided during a Fartlek Interval workout or any other type of workout.

In some embodiments, performance metadata may be based at least partially on a phase of an exercise plan. As previously discussed with respect to block 330 of process 300, performance metadata may be based at least partially on the phase of an exercise plan a user is performing when her performance is monitored (e.g., warm-up, cool down, intense period, recovery period). In some embodiments, a database can include different fields of performance metadata corresponding to different phases of exercise plans. Accordingly, each record may include different metadata representing how the associated media piece affects the user's workout performance when it is provided during different phases of exercise plans. For example, each record may include metadata representing how a media piece affects the user's workout performance when it is provided during a warm-up phase, a cool-down phase, or any other phase of an exercise plan.

Performance metadata stored in database 400 can be based on the workout performance of an individual user or multiple users. In some embodiments, database 400 can include one or more fields for storing performance metadata based on the workout performance of an individual user (see, e.g., block 330 of process 300). For example, the performance metadata stored in fields 482 and/or 484 may be based on the workout performance of a single user. In some embodiments, database 400 can include one or more fields for storing collective performance metadata based, on the workout performances of multiple users (see, e.g., block 340 of process 300). For example, the performance metadata stored in fields 482 and/or 484 may be collective metadata based on the workout performances of multiple users. As previously discussed in connection with block 340 of process 300, there are several techniques for combining performance metadata in accordance with various embodiments.

While database 400 include six records and nine fields, it is understood that any number of records or fields can be provided. For example, database 400 can include enough records to represent all of the media pieces in a library or all of the media pieces offered for sale in a digital music store such as the iTunes Store® offered by Apple Inc., of Cupertino, Calif. Moreover, database 400 can include additional fields representing identification metadata, attribute metadata, performance metadata, any other type of metadata, or any combination thereof.

In some embodiments, performance metadata may include information about two or more different segments within a media piece. For example, performance metadata may include a different workout performance measurement for each segment of a media piece (e.g., each five second segment). FIG. 5 is a schematic view of database 500 for storing performance metadata in accordance with one embodiment of the invention. Database 500 can be stored on any suitable device (e.g., device 100 or devices 220-224) or any suitable server (e.g., server 210). In some embodiments, different devices or servers may store different versions of database 500 (e.g., master and/or local versions). Database 500 can be substantially similar to database 400 shown in FIG. 4 and the description of the latter can be generally applied to the former. For example, database 500 can include records 501-506 (see, e.g., records 401-406 of database 400) and fields 510, 520, 530, 540, 550, 560, and 570 (see, e.g., fields 410, 420, 430, 440, 450, 460, and 470). Moreover, database 500, like database 400, can be used to store metadata based on the workout performance of a single user (see, e.g., block 330 of process 300) or collective metadata based on the workout performances of multiple users (see, e.g., block 340 of process 300).

However, unlike database 400, database 500 can include fields for storing performance metadata associated with different segments of a media piece. For each segment of a media piece, database 500 can include one or more fields for storing performance metadata based on workout performance during that segment. For example, database 500 can include group 580 of fields 582 and 584 based on workout performance during a first segment of a media piece and group 590 of fields 592 and 594 based on workout performance during a second segment of the media piece. While FIG. 5 only shows performance metadata associated with two segments of a media piece, it is understood that performance metadata associated with any suitable number of segments can be stored in a database. Fields in database 500 may store performance metadata that is substantially similar, with the exception of the division of media pieces into segments, to fields in database 400. For example, fields 582 and 592 may store performance metadata representing the pace of one or more users (see, e.g., field 482 of database 400). In another example, fields 584 and 594 may store performance metadata representing the performance of one or more users relative to their targets (see, e.g., field 484 of database 400).

In some embodiments, a media piece may be divided into any suitable number of segments for generating performance metadata associated with each segment. The number of segments that a media piece is divided into may determine the resolution of the performance metadata. In some situations, it may be advantageous to use a relatively large number of segments because it may allow the associated performance metadata to represent workout performance at a relatively high resolution. However, a device may be unable to accurately measure workout performance if each segment is unreasonably short (e.g., less than one second) because there are too many segments in a media piece. Moreover, a device may be unable to calculate and/or store all of the performance metadata if there are too many segments in a media piece. Several approaches can be used to determine the number of segments in a media piece.

In some embodiments, the number of segments may be based on the length of the media piece. For example, a user may specify a particular segment duration (e.g., five seconds) and the number of segments in a media piece may be based on how many segments of that duration the media piece can accommodate. In such embodiments, database 400 may include a substantially large number of performance metadata fields to accommodate the longest media pieces with the most segments.

In some embodiments, the number of segments may be fixed for all media pieces. For example, a user may specify a particular number of segments for all media pieces (e.g., ten segments) and each media piece may be divided into that number of segments. In such embodiments, a database of metadata (see, e.g., database 500) may include fields for specifying the beginning of each segment.

In some embodiments, the number of segments may be based on the content of a media piece. The number of segments may correspond to the number of distinct sections in the media piece. For example, a media piece may be divided into four segments if it includes four distinct sections and each section, has different content (e.g., an introduction, a main portion, a climax, and an ending). Any suitable feature of content can be used to identify transitions between distinct sections. For example, changes in average energy, volume, frequency composition, or any other suitable feature, or any combination thereof may be used to identify transitions between distinct sections of an audio piece. For example, the average energy of a media piece may be used to identify the transition from a song's introduction which primarily includes speech to a song's main body which includes many instruments and singing. In embodiments where the number of segments can be based on the number of distinct sections in a media piece, a database of metadata (see, e.g., database 500) may include fields for specifying the beginning of each segment.

In some embodiments, the number of segments may be based on the workout performance monitored when the media piece is provided. For example, if the workout performance of one or more users changes substantially at a particular point in a media piece, a different segment can be used to represent the effectiveness of that portion of the media piece. In such embodiments, like in some of the previously discussed embodiments, a database of metadata (see, e.g., database 500) may include fields for specifying the beginning of each segment.

In some embodiments, performance metadata representing a collection of media pieces may be stored in a database. For example, a database (see, e.g., database 400 of FIG. 4 or database 500 of FIG. 5) may include a record representing a collection of media pieces (e.g., a playlist) and the record may include performance metadata representing workout performance associated with the collection. In some embodiments, performance metadata can represent average workout performance over an entire collection of media pieces (e.g., one or more users' average workout performance over an entire playlist). In some embodiments, performance metadata can represent workout performance during each media piece in a collection (e.g., one or more users' workout performance during each song in a playlist). For example, a database may include fields for storing performance metadata associated with different segments (see, e.g., database 500 of FIG. 5), and each segment may represent a media piece in a collection (e.g., a song in a playlist). Accordingly, performance metadata may represent the effectiveness of different media pieces in the context of the collection (e.g., the effectiveness of a song when it is provided in a particular playlist order). In some embodiments, performance metadata representing a collection of media pieces can be used to modify the collection and make it more effective for workouts. For example, an ineffective song can be removed from a playlist or moved to a different order in the playlist.

In some embodiments, performance metadata may be based at least partially on user feedback. A device may prompt a user to provide a user input (e.g., feedback) related to a workout after the device has monitored the user's workout performance. For example, a device may prompt a user to evaluate the quality of a workout or the effectiveness of media provided during a workout.

In some embodiments, the monitored workout performance and received user input (e.g., feedback) may be used to generate performance metadata. For example, the performance metadata may reflect if a user indicates that the workout was of a poor quality or if the media piece was inappropriate for the workout. In come embodiments, a measurement of the user's workout performance may be adjusted based on received user input when generating performance metadata. In some embodiments, performance metadata may include a separate metric for received user input (e.g., feedback). For example, a metadata database (see, e.g., database 400 or database 500 may include separate fields for representing user feedback. In some embodiments, performance metadata may be erased or may not be generated at all in response to negative user input.

In some embodiments the monitored workout performance and received user input (e.g., feedback) may affect the manner in which performance metadata is combined with collective performance metadata. For example, the performance metadata based on the user's workout performance (see, e.g., block 330 of process 300) may be weighted based on the user feedback when it is combined with collective performance metadata (see, e.g., block 340 of process 300).

Figure 6:
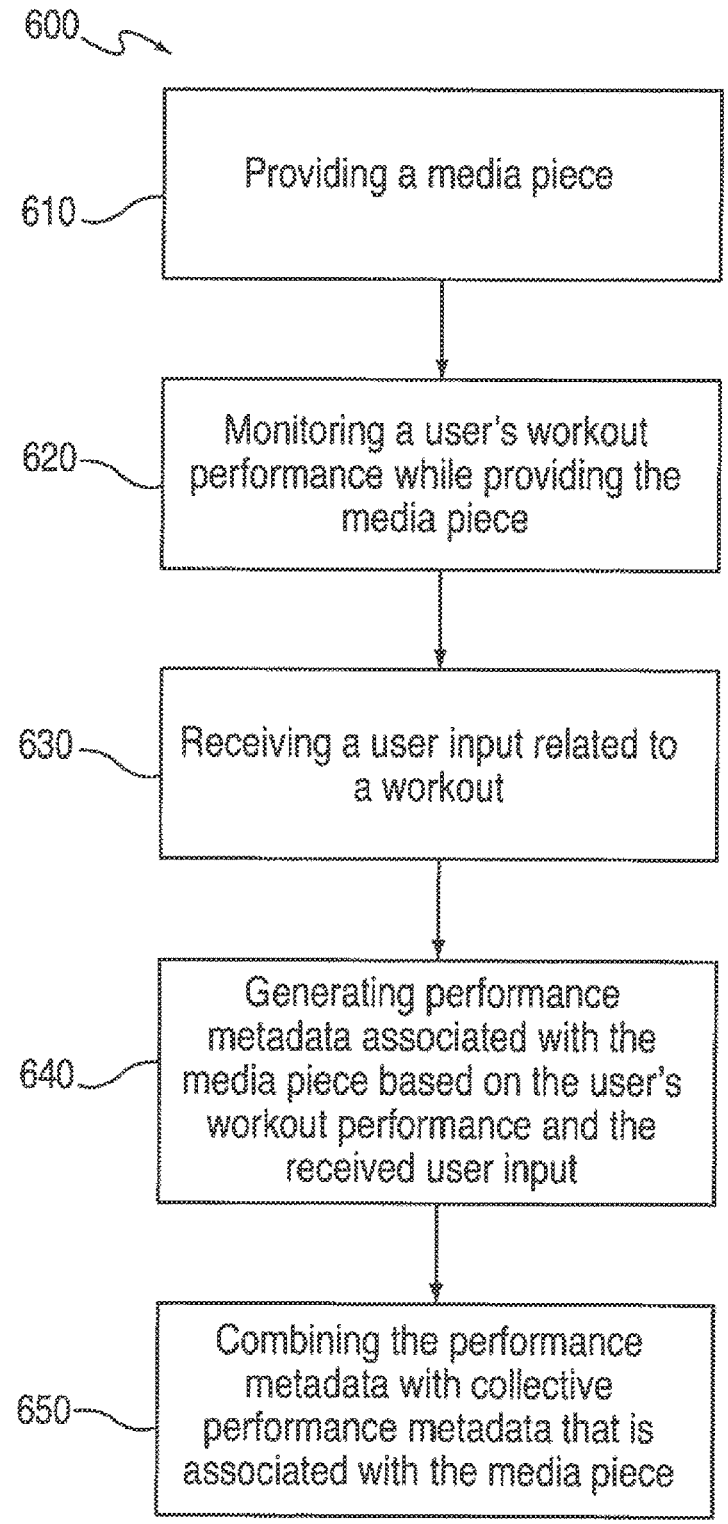
FIG. 6 is a flowchart of an illustrative process for generating performance metadata in accordance with one embodiment of the invention.

FIG. 6 is a flowchart of illustrative process 600 for generating performance metadata in accordance with one embodiment of the invention. Process 600 can be performed by a single device (e.g., device 100 or one of devices 220-224), multiple devices (e.g., two of devices 220-224), a server and a device (e.g., server 210 and one of devices 220-224), or any suitable combination of servers and devices. Process 600 can begin at block 610. Block 610 and block 620 can be substantially similar to, respectively, block 310 and block 320 of process 300, and the previous description of the latter can be applied to the former.

At block 630, a user input can be received related to a workout. For example, a user input can be received related to the workout performed by the user while the media device was provided. The user input can be received through any suitable input mechanism (see, e.g., input/output circuitry 108 of device 100). In some embodiments, a user may be prompted to provide a user input. For example, a device can use a display to present a user with different potential inputs related to a workout (e.g., great workout, great music, neutral, bad workout, and bad music) and the user can select one of the potential inputs.

A user input related to a workout can include any suitable user feedback related to the workout. In some embodiments, the user input can represent the overall quality of the user's workout. While user feedback about the quality of a workout may be indicative of the effectiveness of one or more media pieces provided during the workout, it may not be directly representative of the effectiveness of the one or more media pieces. In some embodiments, the user input can represent the effectiveness of one or more media pieces provided during the workout. However, it may be easier and more natural for some users to provide feedback about the overall quality of a workout rather than feedback about the effectiveness of one or more media pieces. Moreover, feedback about the overall quality of a workout may be used in other contexts beyond workout performance metadata associated with media pieces. For example, feedback about the overall quality of a workout may be used to generate exercise plans to reach long-term exercise or fitness goals. In some embodiments, a user can provide inputs that represent both the overall quality of a workout as well as the effectiveness of one or more media pieces.

In some embodiments, a user input can be received after an entire workout is completed. For example, a user may provide feedback about the entire workout or all of the media pieces provided during the workout. Continuing the example, such a user input may influence performance metadata associated with all of the media pieces provided during the workout.

In some embodiments, user inputs can be received at multiple points during a workout. For example, a user may be prompted to provide feedback after or while each media piece is provided. Continuing the example, such a user input may then affect performance metadata associated with the media piece provided immediately prior to or at the time when the input is received. In another example, a user may be prompted to provide feedback after completing a portion of a workout (e.g., based on a time interval or a workout goal) for which two or more media pieces were provided. Continuing the example, such a user input may affect performance metadata associated with the media pieces provided during that portion of the workout.

At block 640, performance metadata associated with the media piece (see, e.g., block 610) may be generated based on the user's workout performance and the received user input. As previously discussed, there are several ways that performance metadata can be based on received user input (e.g., feedback). In some embodiments, the user's workout performance may be adjusted based on a received user input when generating performance metadata. For example, the user's workout performance relative to her target may be adjusted based on her assessment of the workout quality (e.g., workout performance that exceeds a target may only result in neutral performance metadata if the user provides a poor assessment of the workout's quality). In some embodiments, performance metadata may include a separate metric for user feedback. For example, database 400 or database 500 may include one or more separate fields for storing metadata representing user feedback. In some embodiment, performance metadata may be erased or may not be generated at all in response to received user input (e.g., feedback). For example, no performance metadata may be generated if a user provides strong negative feedback.

In embodiments where performance metadata may be generated for each segment of a media piece (see, e.g., database 500), a received user input may only affect performance metadata related to particular segments of a media piece. For example, user feedback may only affect performance metadata related to segments which were provided to the user (see, e.g., block 610). In some embodiments, received user input may affect performance metadata associated with the entire media piece even though other performance metadata may only be associated with particular segments of a media piece.

At block 650, performance metadata can be combined with collective performance metadata that is associated with the media piece. The performance metadata can be combined with collective performance metadata by any suitable device (see, e.g., device 100 or devices 220-224). As previously discussed, the collective performance metadata may represent the workout performance of other users in response to the media piece (e.g., how other users reacted to the media piece). Combining the performance metadata with collective performance metadata may generate new collective performance metadata that also represents the monitoring performed at block 620. In some embodiments, block 650 may be substantially similar to block 340 of process 300, and the previous description of the latter can be applied to the former.

In some embodiments, performance metadata can be combined with collective performance metadata based at least partially on user input (e.g., feedback). For example, performance metadata based on a user's workout can be combined, based at least partially on feedback from the user, with collective metadata that is based on the workout performance of other users. In some embodiments, performance metadata based on a user's workout can be weighted based on the received user input when it is combined with collective performance metadata. For example, performance metadata based on the user's workout performance relative to her target (see, e.g., fields 464, 584, and 594) may be combined with collective performance metadata based on her assessment of the workout quality (e.g., positive performance metadata may not have a substantial effect on collective performance metadata if the user provides a poor assessment of the workout's quality). In some embodiments, performance metadata based on a user's workout may not even be combined with collective performance metadata if the received user input indicates that the workout quality was unreasonably low or the media pieces were generally ineffective.

In some embodiments, process 600 can include uploading information about a user's workout performance and received user input (e.g., feedback) to a server (see, e.g., server 210) at any point after block 630. Moreover, block 640 and/or block 650 can be performed by the server in some embodiments. For example, process 600 can include uploading information about a user's workout performance and received user input (e.g., feedback) to a server after block 630, and block 640 and block 650 may be performed by the server. In another example, process 600 can include uploading performance metadata and received user input (e.g., feedback) to a server after block 640, and block 650 may be performed by the server. In some embodiments, it may be advantageous for a server to perform block 650 because the server may coordinate or have stored thereon a master version of collective performance metadata.

In some embodiments, one or more media pieces can be selected for a workout based on performance metadata associated with the media pieces. Any suitable type of performance metadata can be used to select media pieces for a workout. For example, performance metadata that represents the past workout performance of a particular user may be used to select media pieces. In another example, collective performance metadata that represents the past performances of multiple users may be used to select media pieces.

In some embodiments, a user may be currently performing a workout and one or more media pieces can be selected, based on performance metadata, that correspond to the user's performance in the current workout. For example, performance metadata can be used to select a media piece that matches a user's current performance level (e.g., running pace). A detailed description of suitable techniques for measuring a user's workout performance (e.g., body metric) for the purposes of selecting music can be found in U.S. Pat. No. 7,521,623, entitled "Music Synchronization Arrangement" and filed on Nov. 24, 2004, which is incorporated by reference herein in its entirety.

In some embodiments, a user may specify an exercise plan (e.g., an exercise activity profile) and one or more media pieces can be selected, based on performance metadata, that correspond to the selected plan. For example, a user may specify an exercise activity profile that includes a warm-up period of medium intensity and than an interval of high intensity and performance metadata can be used to select one or more media pieces for a workout playlist corresponding to the profile. A more detailed description of suitable exercise activity profiles and methods for selecting music based on a profile can be found in U.S. Pat. No. 7,521,623, entitled "Music Synchronization Arrangement" and filed on Nov. 24, 2004, which is incorporated by reference herein in its entirety.

Figure 7:
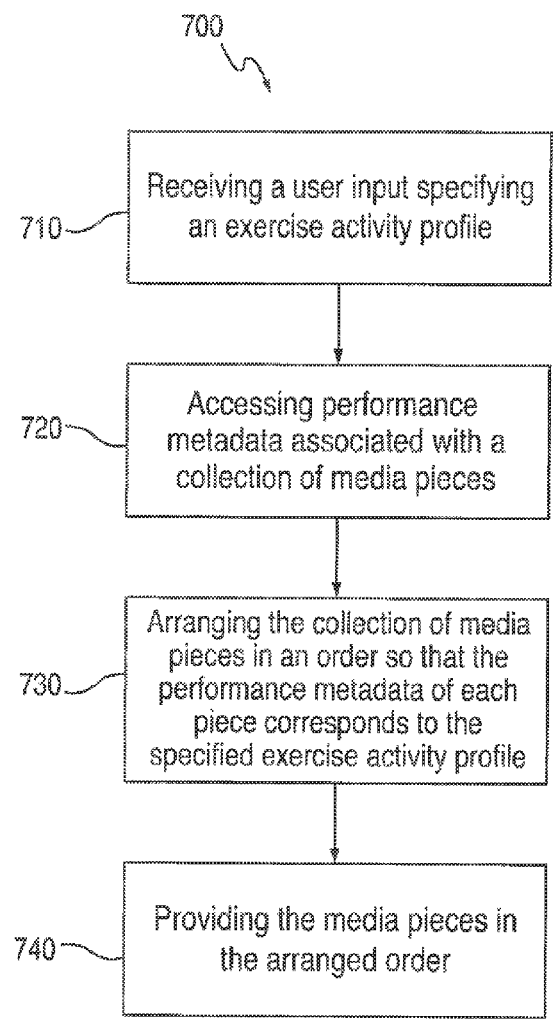
FIG. 7 is a flowchart of an illustrative process for selecting media pieces based on performance metadata in accordance with one embodiment of the invention.

FIG. 7 is a flowchart of illustrative process 700 for selecting media pieces based on performance metadata in accordance with one embodiment of the invention. Process 700 can be performed by a single device (e.g., device 100 or one of devices 220-224), multiple devices (e.g., two of devices 220-224), a server and a device (e.g., server 210 and one of devices 220-224), or any suitable combination of servers and devices. Process 700 can begin at block 710. At block. 710, a user input can be received specifying an exercise activity profile (e.g., an exercise plan). For example, a device can use a display to present a user with different potential activity profiles (e.g., interval training or hill training) and the user can select one of the potential activity profiles.

At block 720, performance metadata associated with a collection of media pieces may be accessed. The collection of media pieces may be selected from any suitable collection of media pieces. For example, the collection of media pieces may include all of the media pieces in a library (e.g., all of the media pieces stored on a user's device). In another example, the collection of media pieces may include only a subset of media pieces specified by a user (e.g., all of the media pieces in a playlist). The performance metadata accessed at block 720 can include any suitable performance metadata. As previously discussed, performance metadata can include metadata based on an individual user's workout performance or collective metadata based on the workout performances of multiple users. In some embodiments, performance metadata accessed at block 720 can include performance metadata associated with different segments of a media piece (see, e.g., group 580 and group 590 of database 500).

At block 730, the collection of media pieces can be arranged in an order so that the performance metadata of each piece corresponds to the specified exercise activity profile. For example, the collection of media pieces can be arranged, in an order so that average pace metadata of each media piece (see, e.g., field 482 of database 400) matches one or more pace targets in the specified exercise activity profile. In some embodiments, the performance metadata of media pieces may not necessarily match one or more pace targets in a specified profile, but media pieces can be arranged based on the closest performance metadata values.

In some embodiments, arranging the collection of media pieces may include specifying portions of a media piece. For example, arranging the collection of media pieces may include specifying starting points and ending points of one or more media pieces. In some embodiments, a media piece may be cutoff if a target specified by an exercise activity profile changes. For example, if an exercise activity profile transitions from a high-intensity section to a low-intensity section, a media piece may be interrupted so that a media piece with more appropriate performance metadata may be provided. In embodiments where per metadata may be generated for each segment of a media piece (see, e.g., database 500), arranging the collection of media pieces may include identifying segments of media pieces with performance metadata that corresponds to the specified profile. For example, the main portion, of a song may be identified even though the introduction of the song may not have enough energy. In such embodiments, any suitable technique may be used to prevent over-editing media pieces because an arrangement of media pieces with too many transitions can be distracting. For example, there may be a limit on the minimum portion of a song that may be identified.

In some embodiments, media pieces with performance metadata indicating that they are not effective for workouts may be moved to the and of an arrangement or completely removed from the arrangement. Any suitable performance metadata for determining if a media piece is ineffective may be used. For example, performance metadata that directly represents user feedback may be used to determine if a media piece is ineffective. In another example, performance metadata that represents workout performance relative to a target may be used to determine if a media piece is ineffective (see, e.g., field 484 of database 400 and fields 584 and 594 of database 500).

At block 740, the media pieces can be provided in the arranged order. For example, the media pieces can be provided to a user in the arranged order during her workout. Any suitable output component in a device (see, e.g., device 100 or one of devices 220-224) can be used to provide media pieces in the arranged order. For example, the media piece can be provided through one or more speakers integrated into the device, one or more speakers coupled with the device, headphones coupled with the device, a display integrated into the device, one or more displays coupled with the device, any other suitable input/output circuitry, or any combination thereof.

In embodiments where an arrangement includes one or more portions of media pieces, providing the media pieces can include providing the corresponding portions of the media pieces in the arranged order. For example, a device may provide the beginning of a first media piece and then, prior to that media piece ending, transition to providing a second media piece based on the arranged order (e.g., bypassing the end of the first media piece). In another example, a device may provide a first media piece and then transition to a middle portion of a second media piece based on the arranged order (e.g., bypassing the beginning of the second media piece).

A device may provide any suitable audio effect to transition between media pieces, portions of media pieces, or any combination thereof. In some embodiments, a device may crossfade from one media piece to another media piece. In some embodiments, a device may use a beat-matching algorithm to temporarily adjust and match the timing of one or both media pieces when transitioning between the media pieces.

The various embodiments of the invention may be implemented by software, but can also be implemented in hardware or a combination of hardware and software. The invention can also be embodied as computer readable code on a computer readable medium. The computer readable medium can be any data storage device that can store data which can thereafter be read by a computer system. Examples of a computer readable medium include read-only memory, random-access memory, CD-ROMs, DVDs, magnetic tape, and optical data storage devices. The computer readable medium can also be distributed over network-coupled computer systems so that the computer readable code is stored and executed in a distributed fashion.

The above described embodiments of the invention are presented for purposes of illustration and not of limitation, and the present invention is limited only by the claims which follow.

What is claimed is:

1. A method for selecting media pieces based on performance metadata, the method comprising:

receiving a user input specifying an exercise activity profile having a plurality of activity intervals, wherein each of the activity intervals has a respective performance target;

accessing collective performance metadata associated with a plurality of media pieces, wherein the collective performance metadata represents combined workout performances of multiple users in response to each of the plurality of media pieces, and wherein the collective performance metadata includes a comparison measure representing a difference between a performance target of an activity interval and a combined workout performance value representing a combination of individual workout performance values of the multiple users in response to a media piece being provided during the activity interval;

arranging the plurality of media pieces in an order corresponding to the activity intervals in the exercise activity profile, wherein the media piece is arranged in the order based on the comparison measure; and providing the plurality of media pieces in the arranged order.

2. The method of claim 1, wherein the comparison measure represents combined workout performances of the multiple users in response to a segment of the media piece.

3. The method of claim 2, wherein the arranging comprises:

specifying the segment of the media piece as corresponding to the activity interval in a sequence based on the comparison measure corresponding to the performance target of the activity interval.

4. A machine readable non-transitory storage medium storing executable instructions which when executed cause a data processing system to perform a method for selecting media pieces based on performance metadata, the method comprising:

receiving a user input specifying an exercise activity profile having a plurality of activity intervals, wherein each of the activity intervals has a respective performance target;

accessing collective performance metadata associated with a plurality of media pieces, wherein the collective performance metadata represents combined workout performances of multiple users in response to each of the plurality of media pieces, and wherein the collective performance metadata includes a comparison measure representing a difference between a performance target of an activity interval and a combined workout performance value representing a combination of individual workout performance values of the multiple users in response to a media piece being provided during the activity interval;

arranging the plurality of media pieces in an order corresponding to the activity intervals in the exercise activity profile, wherein the media piece is arranged in the order based on the comparison measure; and providing the plurality of media pieces in the arranged order.

5. The medium of claim 4, wherein the comparison measure represents combined workout performances of the multiple users in response to a segment of the media piece.

6. The medium of claim 5, wherein the arranging comprises:

specifying the segment of the media piece as corresponding to the activity interval in a sequence based on the comparison measure corresponding to the performance target of the activity interval.

7. A data processing system comprising a processing system coupled to a memory and the memory containing program instructions which configure the processing system to:

receive a user input specifying an exercise activity profile having a plurality of activity intervals, wherein each of the activity intervals has a respective performance target;

access collective performance metadata associated with a plurality of media pieces, wherein the collective performance metadata represents combined workout performances of multiple users in response to each of the plurality of media pieces, and wherein the collective performance metadata includes a comparison measure representing a difference between a performance target of an activity interval and a combined workout performance value representing a combination of individual workout performance values of the multiple users in response to a media piece being provided during the activity interval;

arrange the plurality of media pieces in an order corresponding to the activity intervals in the exercise activity profile, wherein the media piece is arranged in the order based on the comparison measure; and providing the plurality of media pieces in the arranged order.

8. A method for selecting media pieces, the method comprising:

receiving an input specifying an exercise activity profile having a plurality of activity intervals, wherein each of the activity intervals has a respective performance target;

accessing first performance metadata associated only with a first media piece;

accessing first collection performance metadata associated with a first collection of media pieces comprising at least the first media piece and a second media piece arranged in a first order, wherein the first collection performance metadata represents combined workout performances of multiple users in response to the first media piece and the second media piece, and wherein the collection performance metadata includes a comparison measure representing a difference between a performance target of an activity interval and a combined workout performance value representing a combination of individual workout performance values of the multiple users in response to a first media segment of the first media piece being provided during the activity interval; and arranging a second collection of media pieces in a second order corresponding to activity intervals in the exercise activity profile based on the exercise activity profile, the first performance metadata, and the first collection performance metadata, wherein the second collection of media pieces includes segments of the first media piece and the second media piece, and wherein the first media segment of the first media piece is arranged in the second order based on the comparison measure.

9. The method of claim 8, wherein the first media piece comprises a second media piece segment, and wherein the second order comprises at least a portion of the second media piece between the first media piece segment and the second media piece segment.

10. The method of claim 8 further comprising providing the second collection of media pieces in the second order.

11. The method of claim 10, wherein the providing comprises crossfading between two media pieces of the second collection of media pieces in the second order.

12. The method of claim 10, wherein the providing comprises using a beat-matching algorithm to match the timing of two media pieces of the second collection of media pieces in the second order.

13. The method of claim 8, wherein the receiving comprises receiving the input from a particular user.

14. The method of claim 13, wherein the first performance metadata includes a performance measure representing a past workout performance of the particular user.

15. A machine readable non transitory storage medium storing executable instructions which when executed cause a data processing system to perform a method for selecting media pieces, the method comprising:

receiving an input specifying an exercise activity profile having a plurality of activity intervals, wherein each of the activity intervals has a respective performance target;

accessing first performance metadata associated only with a first media piece;

accessing first collection performance metadata associated with a first collection of media pieces comprising at least the first media piece and a second media piece arranged in a first order, wherein the first collection performance metadata represents combined workout performances of multiple users in response to the first media piece and the second media piece, and wherein the collection performance metadata includes a comparison measure representing a difference between a performance target of an activity interval and a combined workout performance value representing a combination of individual workout performance values of the multiple users in response to a first media segment of the first media piece being provided during the activity interval; and arranging a second collection of media pieces in a second order corresponding to activity intervals in the exercise activity profile based on the exercise activity profile, the first performance metadata, and the first collection performance metadata, wherein the second collection of media pieces includes segments of the first media piece and the second media piece, and wherein the first media segment of the first media piece is arranged in the second order based on the comparison measure.

16. The medium of claim 15, wherein the first media piece comprises a second media piece segment, and wherein the second order comprises at least a portion of the second media piece between the first media piece segment and the second media piece segment.

17. The medium of claim 15 further comprising providing the second collection of media pieces in the second order.

18. The medium of claim 17, wherein the providing comprises crossfading between two media pieces of the collection of media pieces in the second order.

19. The medium of claim 17, wherein the providing comprises using a beat-matching algorithm to match the timing of two media pieces of the second collection of media pieces in the second order.

20. The medium of claim 19, wherein the receiving comprises receiving the input from a particular user.

21. The medium of claim 20, wherein the first performance metadata is based on a past workout performance of the particular user.

22. A data processing system comprising a processing system coupled to a memory and the memory containing program instructions which configure the processing system to:

receive an input specifying an exercise activity profile having a plurality of activity intervals, wherein each of the activity intervals has a respective performance target;

access first performance metadata associated only with a first media piece;

access first collection performance metadata associated with a first collection of media pieces comprising at least the first media piece and a second media piece arranged in a first order, wherein the first collection performance metadata represents combined workout performances of multiple users in response to the first media piece and the second media piece, and wherein the collection performance metadata includes a comparison measure representing a difference between a performance target of an activity interval and a combined workout performance value representing a combination of individual workout performance values of the multiple users in response to a first media segment of the first media piece being provided during the activity interval; and arrange a second collection of media pieces in a second order corresponding to activity intervals in the exercise activity profile based on the exercise activity profile, the first performance metadata, and the first collection performance metadata, wherein the second collection of media pieces includes segments of the first media piece and the second media piece, and wherein the first media segment of the first media piece is arranged in the second order based on the comparison measure.

* * * * *